(12) United States Patent
Pinkie

(10) Patent No.: US 9,968,383 B2
(45) Date of Patent: May 15, 2018

(54) HOOK INSERTER

(71) Applicant: Alphatec Spine, Inc., Carlsbad, CA (US)

(72) Inventor: Alexandra Pinkie, Vista, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days. days.

(21) Appl. No.: 15/291,344

(22) Filed: Oct. 12, 2016

(65) Prior Publication Data

US 2017/0105769 A1    Apr. 20, 2017

Related U.S. Application Data

(60) Provisional application No. 62/243,399, filed on Oct. 19, 2015.

(51) Int. Cl.
*A61B 17/70*  (2006.01)

(52) U.S. Cl.
CPC ...... *A61B 17/7076* (2013.01); *A61B 17/7001* (2013.01); *A61B 17/7032* (2013.01); *A61B 17/7056* (2013.01)

(58) Field of Classification Search
CPC .................................. A61B 17/7074–17/7098
See application file for complete search history.

(56) References Cited

U.S. PATENT DOCUMENTS

| 4,347,845 | A | 9/1982 | Mayfield |
| 8,133,263 | B2 | 3/2012 | Lewis et al. |
| 2006/0025768 | A1 | 2/2006 | Iott et al. |
| 2007/0161989 | A1 | 7/2007 | Heinz et al. |
| 2008/0183180 | A1 | 7/2008 | Franks et al. |
| 2010/0094358 | A1* | 4/2010 | Moore ............... A61B 17/0642 606/319 |
| 2010/0114182 | A1* | 5/2010 | Wilcox ............... A61B 17/7079 606/86 A |
| 2011/0022088 | A1* | 1/2011 | Forton ............... A61B 17/7086 606/246 |
| 2012/0226316 | A1* | 9/2012 | Dant .................... A61B 17/705 606/250 |
| 2013/0110123 | A1* | 5/2013 | Foirella .............. A61B 17/8872 606/104 |

FOREIGN PATENT DOCUMENTS

| WO | WO 2014009338 A1 * | 1/2014 | ......... A61B 17/7032 |
| WO | WO 2015024976 A1 * | 2/2015 | ......... A61B 17/7086 |

* cited by examiner

*Primary Examiner* — Nicholas Plionis
(74) *Attorney, Agent, or Firm* — Dinsmore & Shohl LLP

(57) ABSTRACT

Instruments and systems for performing spinal fixation are provided. The instruments and system configured to position and force fit a hook onto a pedicle bone. The systems include a hook and an instrument. The instrument includes a handle and a rod fixedly mounted to a distal end of the handle. The instrument includes a hook support portion having a hood. The hood includes an opening, a support wall, a post and a threaded knob. The support wall is configured to support the hook. The post has a bottom surface dimensioned similar to that of a spinal rod. The threaded knob is mounted within the opening of the hood and engages a pair of threaded sidewalls of a rod support portion of the hook so as to pull the hook into a fixed engagement with the post, securing the hook support portion to the post.

12 Claims, 6 Drawing Sheets

HOOK INSERTER

CROSS-REFERENCE TO RELATED APPLICATIONS

This application claims priority of U.S. Provisional Patent Application No. 62/243,399 filed Oct. 19, 2015, the contents of which are incorporated herein by reference.

FIELD OF THE INVENTION

Instruments and systems configured to fix two adjacent vertebrae together are provided.

BACKGROUND OF THE INVENTION

Certain spinal procedures require the fixation of two adjacent vertebrae. In such procedures the fixation may be made by attaching a pair of hooks 100 to pedicle bones of adjacent vertebrae, running a spinal rod (not shown) between the two hooks and securing the hooks to the spinal rod. The prior art figures shown in FIGS. 1A and 1B shows a generic hook and two instruments 200, 300 attached thereto in accordance with the prior art.

The hook 100 has a pedicle receiving portion 102 configured to provide a tensioned engagement with a pedicle bone. In particular, the pedicle receiving portion 102 includes a blade 104 having a back wall 104a so as to form a C-shaped cross section. The C-shaped cross section is configured to form a tension fit with a free end of the pedicle bone.

The hook 100 further includes a rod support portion 108. The rod support portion 108 includes a pair of sidewalls 110a, 110b spaced apart from each other so as to define a channel 112 having a U-shaped cross-section. The channel is configured to receive a portion of the spinal rod. Additionally, the sidewalls 110a, 110b may be threaded so as to receive a set screw for tightening the hook 100 securely onto the spinal rod.

Currently the attachment of the hook to the pedicle bone requires two instruments. One instrument, the insertion instrument 200, engages the side walls 110A, 110B of the hook 100 so as to position the hook 100 onto the pedicle. A second instrument 300, a force translating instrument 300, is configured to apply a force so as to force fit the blade opening onto the pedicle bone.

With reference again to FIG. 1B, a partial view of the two instruments is provided. In particular, the insertion instrument 200 is a pair of forceps which pinches onto opposing side walls 110A, 110B of a rod support portion 106 of the hook 100. The force translating instrument 300 includes a male member 302 with a rod 304 that is seated within the rod support portion 106 of the hook 100. It should be appreciated that the forceps 200 position the hook 100 onto the pedicle bone and the force translating instrument may be used to translate a force from the blow of a hammer so as to fit the blade onto the pedicle bone.

Accordingly, the attachment may require the assistance of two surgeons. One surgeon holds the forceps in place so as to position the hook onto the pedicle whereas the other surgeon may use the hammering tool to force fit the pedicle and the hook together. Accordingly, it remains desirable to simplify the procedure of attaching a hook onto a pedicle bone by utilizing only one surgeon. In particular, it remains desirable to have an instrument configured to both manipulate the hook onto the pedicle bone as well as translate a force onto the pedicle bone to force fit the hook to the pedicle bone.

SUMMARY OF THE INVENTION

An instrument for inserting a hook onto a pedicle is provided. The instrument is configured to both position the hook onto the pedicle bone and apply a force onto the hook so as to force fit the hook onto the pedicle bone. The instrument includes a handle, a rod, and a hook support portion. The rod and the handle are axially aligned.

The hook support portion includes a support surface which is angled relative to the rod so as to translate a load from the rod onto the hook at approximately a 45 degree angle. The hook support portion further includes a post and a hood. The hood is elevated above the post and includes a bore. A threaded knob is rotatably mounted in the bore.

The post is configured to receive a rod support portion of the hook in the same manner as a spinal rod is received by the rod support portion. The threaded end of the threaded knob is configured to threadably engage threaded side walls of the rod support portion of the hook so as to pull and secure the hook to the hook support portion.

Accordingly, a single surgeon may both position the pedicle receiving portion of the hook onto a corresponding pedicle and may translate a force onto the hook so as to force fit the hook onto the pedicle.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings where like structure is indicated with like reference numerals and in which:

DETAILED DESCRIPTION OF THE PREFERRED EMBODIMENTS

An instrument for both positioning and force fitting a hook onto a pedicle bone is provided. In particular, the instrument includes a handle. A rod is fixedly mounted to a distal end of the handle. A proximal end of the handle may be configured to have a rigid surface to absorb a stroke of a hammer.

The distal end of the rod includes a hook support portion. The hook support portion includes a hood having an opening. A support wall is configured to hold a proximal end of a hook. The support wall has a support surface that is generally angled 45 degrees relative to the rod.

The hook support portion further includes a post. The post has a bottom surface having a dimension similar to that of a spinal rod. A threaded knob is mounted within the opening of the hood. The threaded knob is configured to engage the threaded sidewalls of the rod support portion so as to be selectively displaced along its axial length with respect to the hood. The threaded end of the knob is disposed beneath the hood.

In operation the hook may be slid onto the post, wherein the post is seated within the rod support portion. The threaded knob is rotated so as to engage the threaded opening of the hook, wherein the threaded knob engages the threaded sidewalls of the rod support portion of the hook. The threaded knob is turned so as to move towards the post, pinching the post and securing the hook to the instrument. Accordingly, the surgeon can manipulate the hook onto a pedicle and apply a force through the proximal end of the hammer to force fit the hook onto the pedicle.

Figure 1A:
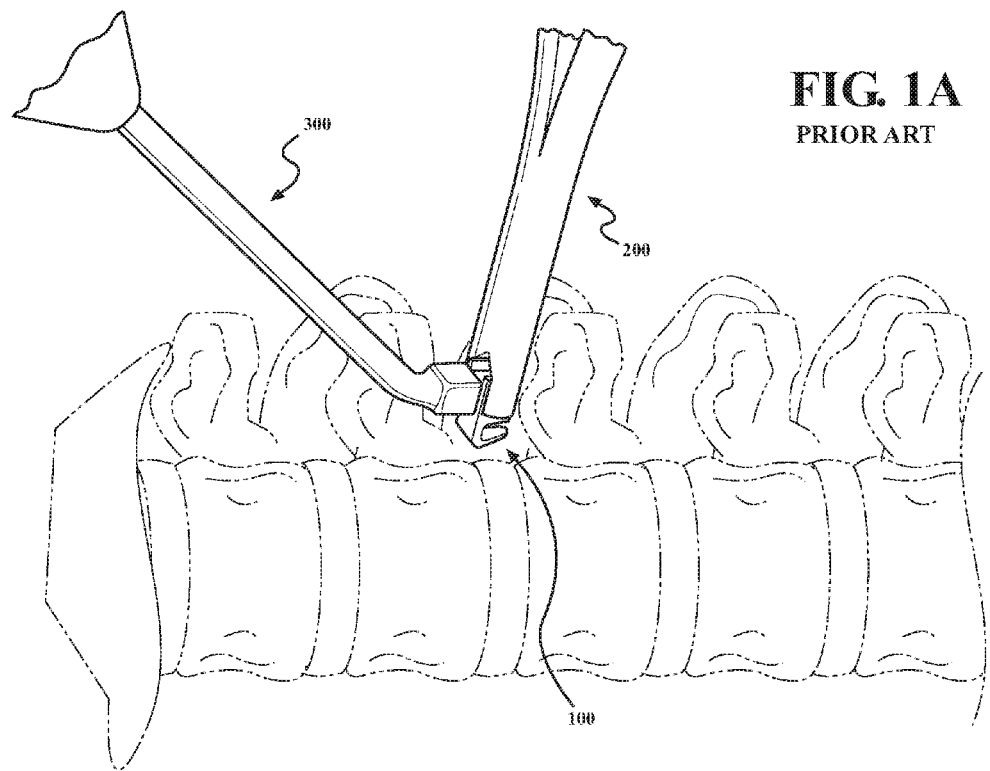
FIG. 1a is a prior art view showing a hook and an insertion instrument for attaching the hook onto a pedicle.
Figure 1B:
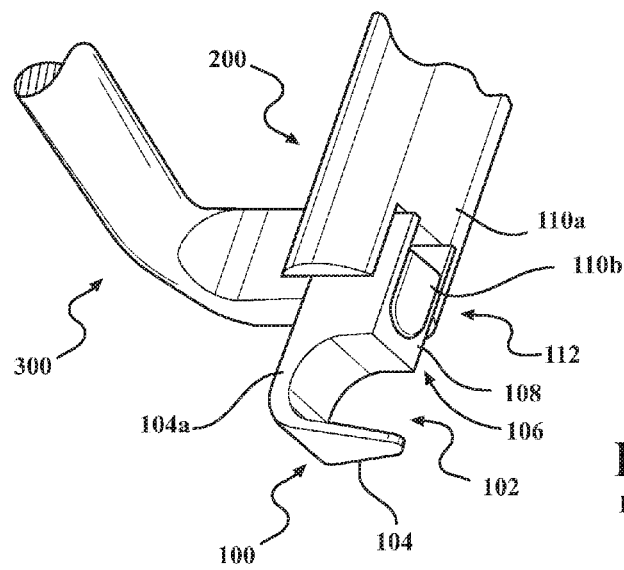
FIG. 1b is a close-up view showing a forceps manipulating the hook onto the pedicle and a force translating instrument for driving and force fitting the hook onto the pedicle.

With reference now to FIGS. 2-5, an illustrative view of the instrument 10 is provided. The instrument 10 is configured to be used with a hook 100 (shown in FIGS. 1B and also 6). Any hook 100 currently known and used in the art may be adapted for use herein.

Figure 10A:
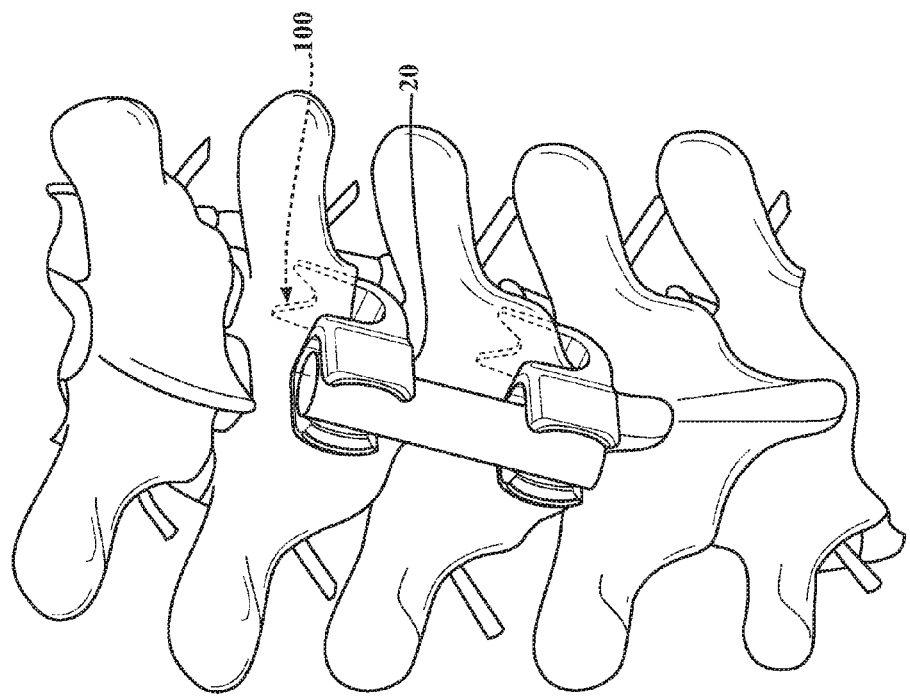
FIG. 10A is close up view of the hook and the instrument shown in FIG. 9 attached to a pedicle bone.
Figure 10B:
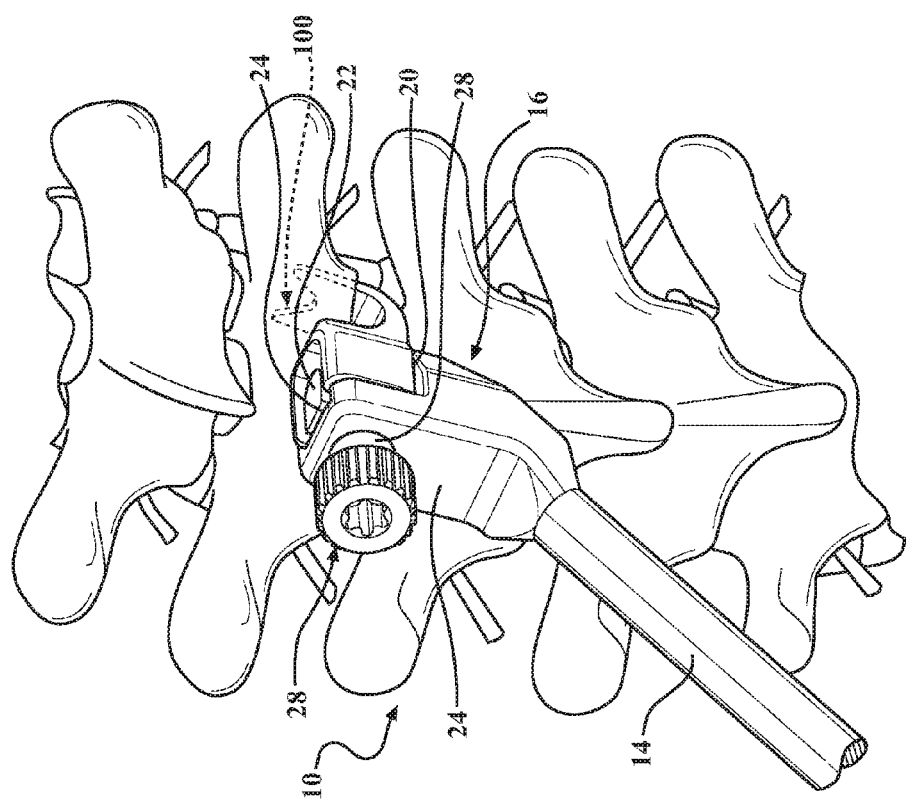
FIG. 10B is a perspective view showing two hooks mounted to adjacent vertebrae with a spinal rod disposed in the channels of the respective hooks.

The hook 100 includes a pedicle receiving portion 102 having a blade 104 and a rod support portion 106. The blade 104 is curved so as to form a generally C-shaped cross section wherein the blade 104 is configured to engage a pedicle bone. The rod support portion 106 is integrally formed to the blade 104 and includes a rod seating portion 108. The rod seating portion 108 is a generally tubular portion configured to receive a spinal rod 400 (as shown in FIG. 10B). The rod support portion 106 further includes a pair of sidewalls 110a, 110b extending upwardly from the rod seating portion 108 and are spaced apart from each other so as to define a channel 112.

The channel 112 provides the rod seating portion 108 with a U-shaped profile. The U-shaped profile of the rod seating portion 108 is on a plane orthogonal to the U-shaped profile of the blade 104. The sidewalls 110a, 110b are threaded so as to receive a set screw (not shown). Thus, a spinal rod 400 is passed through the channel 112 defined by opposing sidewalls 110a, 110b and secured within the rod seating portion 108 by application of a set screw (not shown) so as to hold the spinal rod 400 and the pedicle bone in a fixed position relative to each other. Preferably the spinal rod 400 and the hook support portion 16 are formed from a durable and rigid material suitable for medical use such as titanium.

The instrument 10 includes a handle 12, a rod 14 and a hook support portion 16. The handle 12 is configured to have a diameter to facilitate the grip of a user. A proximal end 12a of the handle 12 may be configured to have a rigid surface to absorb impact from a hammer (not shown). The body 12b of the handle 12 may be formed of a cushioned material so as to mitigate the translation of force from the hammer onto the hand gripping the handle 12. Such material may illustratively include rubber, foam or the like.

The rod 14 extends axially from a center of the handle 12. The rod 14 is formed of a durable and rigid material configured to facilitate the translation of a force from one end of the rod 14 to the other end. Such materials are currently known and used and illustratively include medical grade titanium or steel. In one embodiment, the handle 12 is threadedly engaged with the rod 14. However, it should be appreciated that the rod 14 and the handle 12 may be formed as a single unitary piece.

Figure 2:
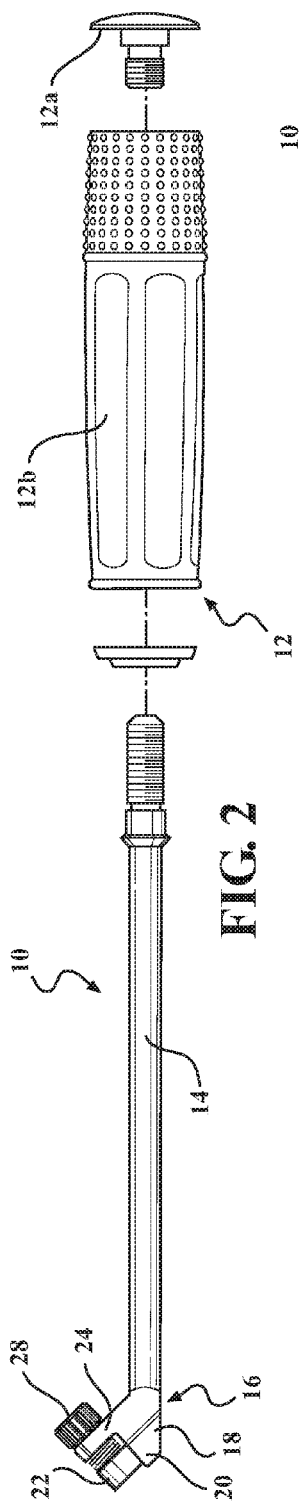
FIG. 2 is a partially exploded view of the instrument taken from the side.
Figure 3:
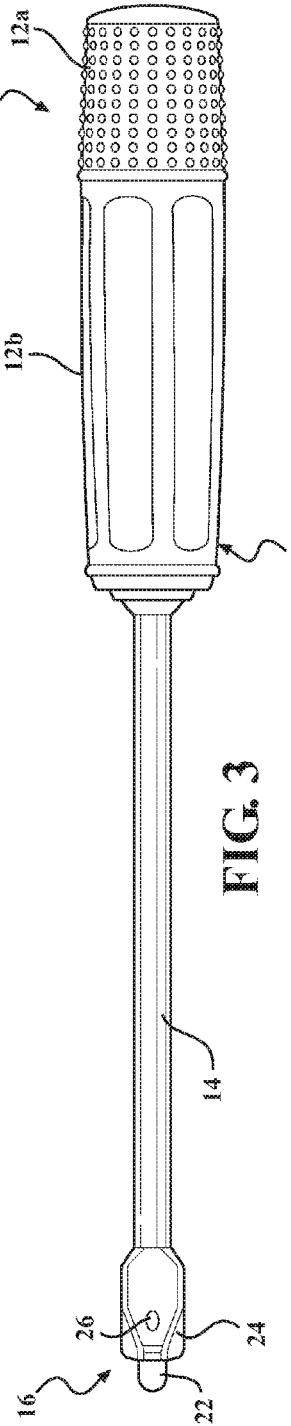
FIG. 3 is a view of the instrument shown in FIG. 2 taken from the bottom.
Figure 4A:
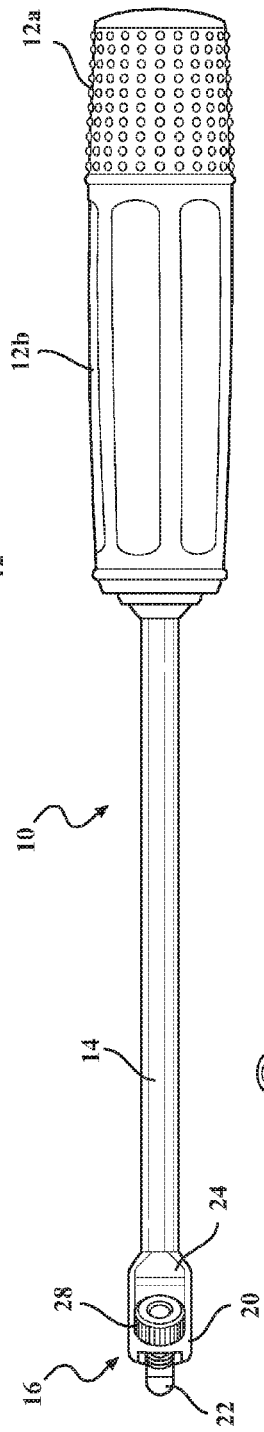
FIG. 4A is a view of the instrument shown in FIG. 2 taken from the top.
Figure 4B:
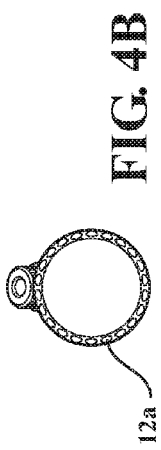
FIG. 4B is a view of the instrument shown in FIG. 2 looking down on the handle.
Figure 5:
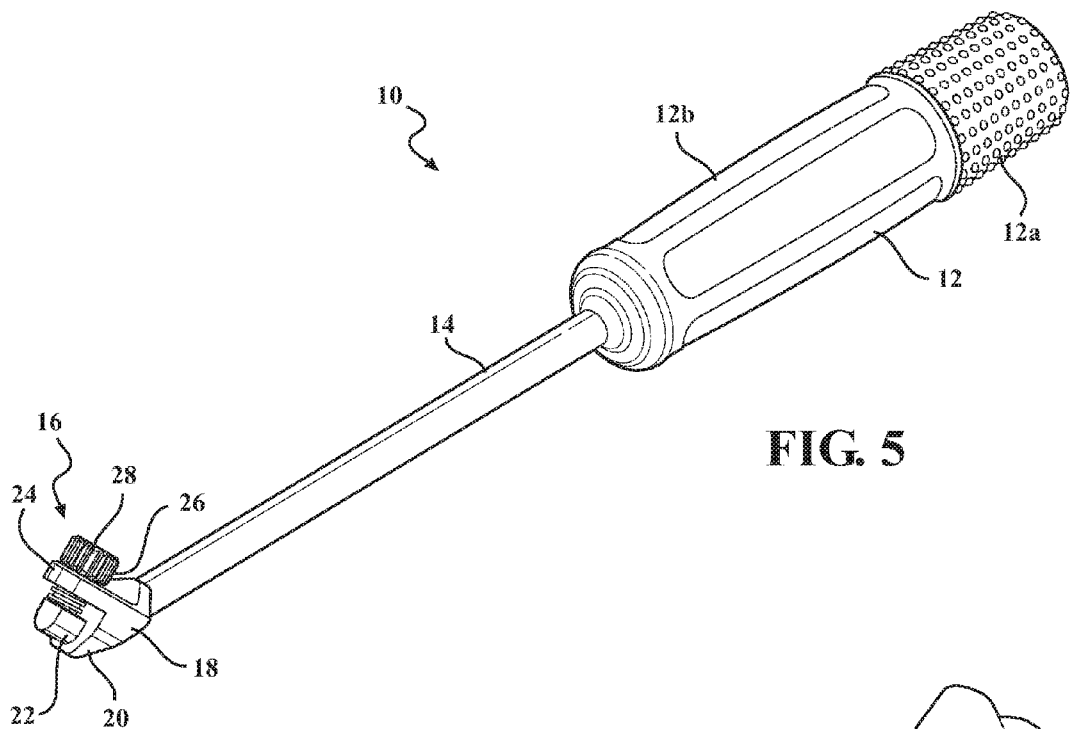
FIG. 5 is a perspective view of the instrument shown in FIG. 2.

The hook support portion 16 is fixedly attached to a distal end of the rod 14. In one embodiment, the hook support portion 16 is integrally formed with the rod 14. The hook support portion 16 is configured to hold the hook 100. The hook support portion 16 is a generally solid member having a pair of support walls 18b and a back surface 18a which is generally coaxial to the rod 14. A support surface 20 is angled relative to the rod 14. For illustrative purposes, the support surface 20 is shown angled relatively 45 degrees with respect to the rod 14, however, it should be appreciated that the support surface 20 may be angled otherwise without deviating from the scope of the appended claims. As shown in FIG. 2, the support surface 20 will hold the hook 100 at a generally 45 degree angle relative to the rod 14.

Figure 6:
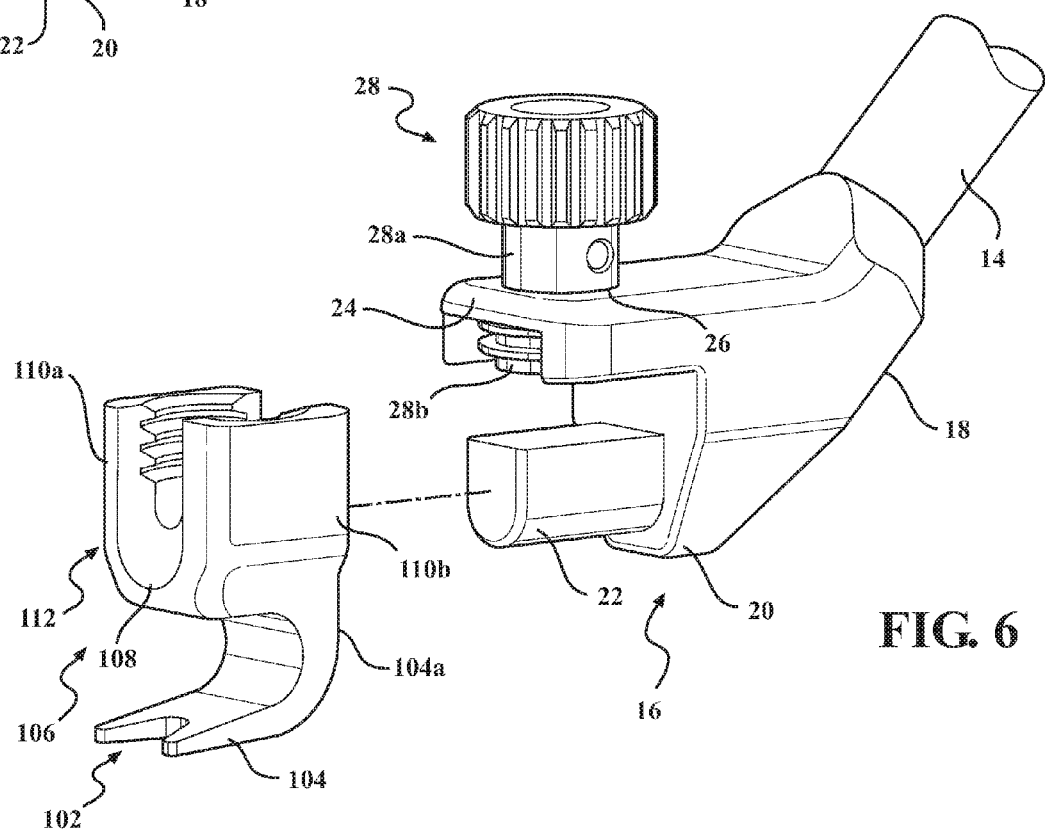
FIG. 6 is a close-up view of the instrument shown in FIG. 2 showing the hook displaced from the instrument.

Looking now at FIG. 6, the hook support portion 16 further includes a post 22. The post 22 is a solid and elongated piece fixedly secured to the support surface 20. The post 22 has a bottom portion dimensioned to assume the shape of the rod 14. In particular, the bottom portion of the post 22 is radiused. The post 22 may have a pair of generally planar side walls 22a opposite each other and a planar top surface 22b and a planar distal end 22c. The post 22 projects generally orthogonal from the support surface 20. The post 22 is dimensioned similar to that of a spinal rod 400 accordingly, the dimensions of the post 22 may be modified based upon the spinal rod used 400 in the procedure.

The hook support portion 16 further includes a hood 24. The hood 24 is a generally rectangular prism in shape and includes an opening 26. The hood 24 is integrally formed to the support wall 18 of the hook support portion 16. The opening 26 has a diameter sufficient to receive a threaded knob 28. In particular, the threaded knob 28 includes a neck 28a and a threaded end 28b. The neck 28a is smooth and has a diameter smaller than that of the opening 26. The threaded end 28b includes threads having a diameter larger than the opening 26 such that the threaded knob 28 is retained to the hood 24. The diameter of the threaded end 28b is configured to replicate the threads of a set screw configured to secure a hook 100 to a spinal rod 400. Accordingly, it should be appreciated that the diameter of the opening 26 may be modified without deviating from the scope of the appended claims based upon the size of the hook 100 being used in the procedure.

In one embodiment, the threaded knob 28 is formed as two pieces assembled together. For instance, the neck 28a and the threaded end 28b may be formed as a single piece. A knob 28c having an opening dimensioned to receive a proximal end of the neck 28a is fixedly mounted to the proximal end of the neck 28a. The knob 28c may include features to facilitate a grip of the knob 28c. In such an embodiment, the neck 28a is passed through the opening 26 and the knob 28c is secured to the proximal end of the neck 28a so as to secure the threaded knob 28 to the hood 24.

Figure 7:
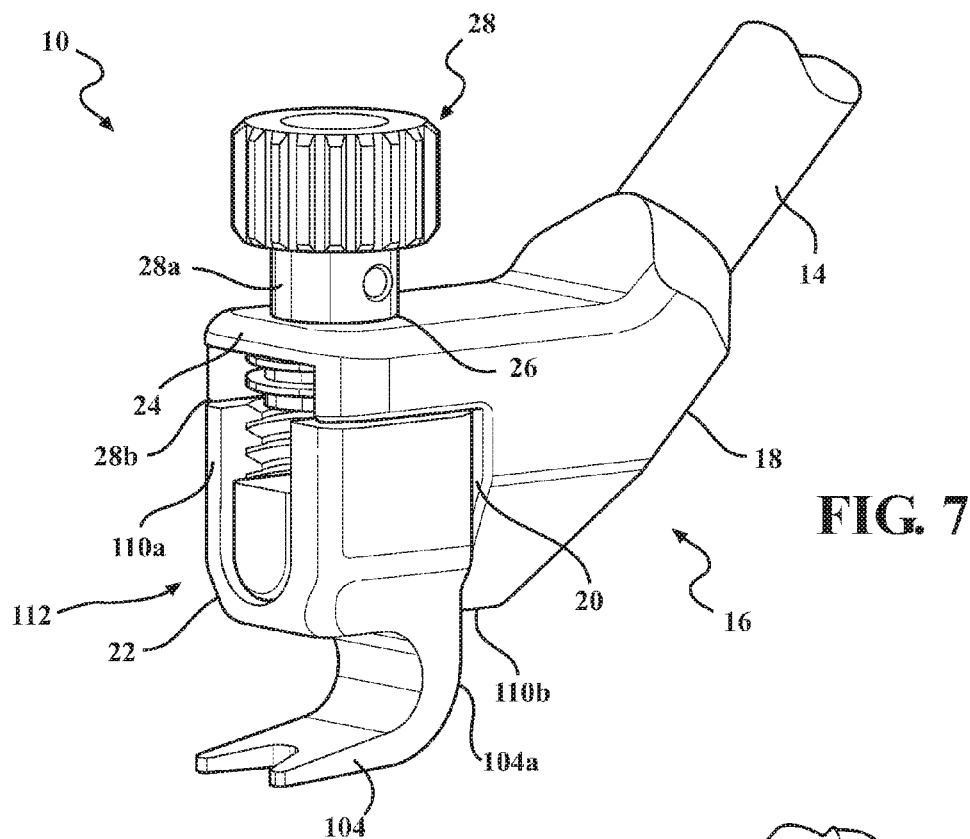
FIG. 7 is a perspective view showing the hook seated on the post.

With reference again to FIG. 6 and now to FIGS. 7-10B, the operation of the instrument 10 is provided. As shown in FIG. 6, the hook 100 is placed onto the hook support portion 16 by seating the rod support portion 106 of the hook 100 to the post 22 of the hook support portion 16. In particular, the post 22 is placed into the channel 112 of the rod seating portion 108 of the rod support portion 106. The threaded end 28b of the threaded knob 28 is aligned with the rod support portion 106 of the hook as shown in FIG. 7 so as to be registered to threadingly engage the threads of the side walls 110a, 110b of the rod support portion 106.

Figure 8:
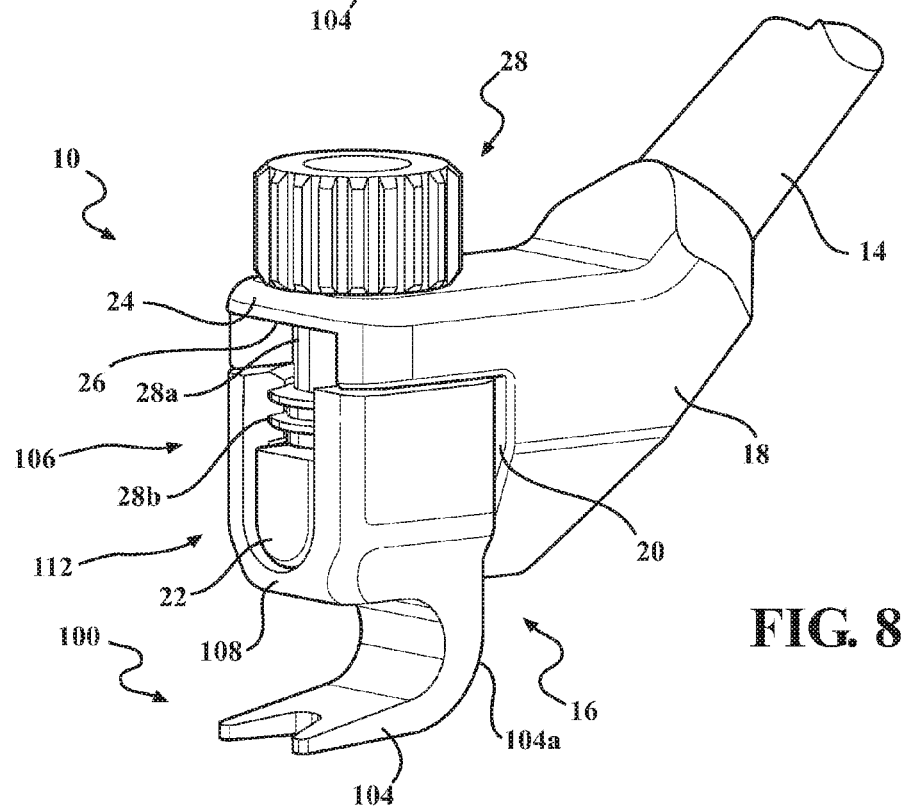
FIG. 8 is a perspective view showing the threads of the knob engaged with the threads of the hook.
Figure 9:
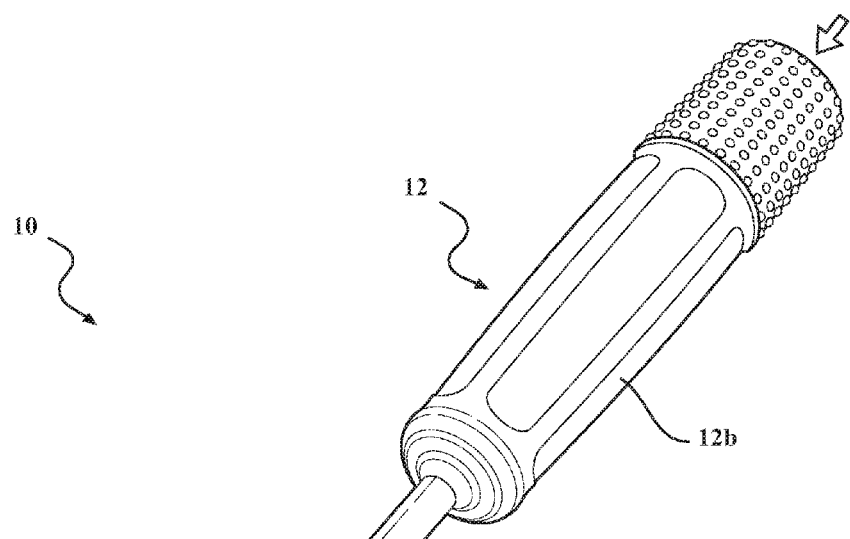
FIG. 9 is a perspective view showing the hook attached to the instrument.
Figure 9:
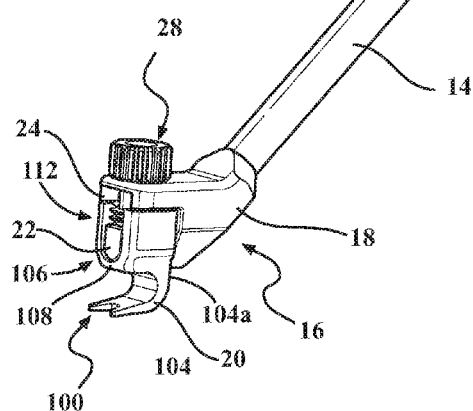

FIG. 8 shows the threaded end 28b of the threaded knob 28 engaged with the the rod support portion 106. In particular, the threaded end 28b of the threaded knob 28 is threadingly engaged with the sidewalls 110a, 110b of the rod support portion 106. The post 22 is seated within the channel 112 of the rod seating portion 108.

The threaded knob 28 is tightened onto the post 22 thus pulling the hook 100 up against an under surface of the post 22 so as to secure the hook 100 to the instrument 10. It should be appreciated that securing the hook 100 to the instrument 10 may be done by a single person. The user can then position the pedicle receiving portion 102 onto the pedicle bone and apply a load (indicated by the arrow shown in FIG. 9) onto the proximal end of the handle 12 by the use of an instrument such a mallet to fully seat the hook 100 onto the pedicle bone (FIG. 10A). In particular, the axial load of the mallet is translated along the rod 14 and onto the hook 100 (FIG. 10A) at an angle of approximately 45 degrees. Once the hook 100 is firmly implanted onto the pedicle bone, the threaded knob 28 can be loosened so as to allow the instrument 10 to disengage from the hook 100 at which point the surgeon may advance the surgical procedure by placing a spinal rod 400 into the rod support portion 106 of the hook 100 and securing the hook 100 to the spinal rod by application of a set screw onto the threaded sidewalls 110a, 110b of the rod support portion 106 as shown in FIG. 10B. FIG. 10B provides a view of a pair of hooks 100 mounted to adjacent vertebrae by attachment to pedicle bones, a spinal rod 400 is seated within the respective channels 112 of the rod support portion 106 of respective hooks 100. Set screws (not shown) may be screwed onto the channels 112 so as to pinch the spinal rod 400 and secure the spinal rod 400 to respective hooks 100.

While particular embodiments have been illustrated and described herein, it should be appreciated that various other changes and modifications may be made without departing from the spirit and scope of the subject matter. Moreover, although various aspects of the claimed subject matter have been described herein, such aspects need not be utilized in combination.

I claim:

1. An instrument configured to position and force fit a hook onto a pedicle bone, the instrument comprising:
    a handle;
    a rod fixedly mounted to a distal end of the handle; and
    a hook support portion fixedly mounted to a distal end of the rod, the hook support portion having a hood extending at an angle from the rod, the hood having an opening, the hook support portion further including a support wall orthogonal to the hood, a post fixedly mounted to the support wall, the post being orthogonal to the support wall and parallel to the hood, and a threaded knob, the support wall configured to support the hook, the post having an arcuate bottom surface; the threaded knob mounted within the opening of the hood, the threaded knob configured to engage a pair of threaded sidewalls of a rod support portion of the hook so as to pull the hook into a fixed engagement with the post, securing the hook support portion to the post, and wherein
    the hood is integral with the support wall and fixed with respect to the support wall.

2. The instrument as set forth in claim 1, wherein a proximal end of the handle includes a rigid surface to absorb impact from a hammer.

3. The instrument as set forth in claim 1, wherein the support wall has a support surface that is generally angled 45 degrees relative to the rod, so as to place the post along an axis 45 degrees relative to the rod.

4. The instrument as set forth in claim 1, wherein the hook support portion is a generally solid member having a pair of support walls and a back surface which is generally coaxial to the rod.

5. The instrument as set forth in claim 1, wherein a bottom portion of the post is radiused such that the bottom surface is convex with respect to the hood.

6. The instrument as set forth in claim 5, wherein the post may have a pair of generally planar side walls opposite each other and a planar top surface and a planar distal end.

7. A system for fixing two adjacent vertebrae together by attaching to a pedicle bone of each of the two adjacent vertebrae to a spinal rod, the system comprising:
    a hook having a pedicle receiving portion and a rod support portion, the pedicle receiving portion having a blade, wherein the blade is curved so as to form a generally C-shaped cross section wherein the blade is configured to engage the pedicle bone, the rod support portion is integrally formed to the blade and includes a rod seating portion, wherein the rod seating portion is a generally tubular portion configured to receive the spinal rod, the rod seating portion further including a pair of sidewalls extending upwardly and are spaced apart from each other so as to define a channel;
    an instrument having a handle, a rod fixedly mounted to a distal end of the handle, and a hook support portion fixedly mounted to a distal end of the rod, the hook support portion having a hood extending at an angle from the rod, the hood having an opening, the hook support portion further including a support wall orthogonal to the hood, a post fixedly mounted to the support wall, the post being orthogonal to the support wall and parallel to the hood, and a threaded knob, the support wall is configured to support the hook, the post having a bottom surface; the threaded knob mounted within the opening of the hood, the threaded knob configured to engage a pair of threaded sidewalls of the rod support portion of the hook so as to pull the hook into a fixed engagement with the post, securing the hook support portion to the post, and wherein
    the hood is integral with the support wall and fixed with respect to the support wall.

8. The system as set forth in claim 7, wherein a proximal end of the handle includes a rigid surface to absorb impact from a hammer.

9. The system as set forth in claim 7, wherein the support wall has a support surface that is generally angled 45 degrees relative to the rod, so as to place the post along an axis 45 degrees relative to the rod.

10. The system as set forth in claim 7, wherein the hook support portion is a generally solid member having a pair of support walls and a back surface which is generally coaxial to the rod.

11. The system as set forth in claim 7, wherein a bottom portion of the post is radiused.

12. The system as set forth in claim 11, wherein the post may have a pair of generally planar side walls opposite each other and a planar top surface and a planar distal end.

* * * * *